United States Patent [19]
Mers Kelly et al.

[11] Patent Number: 6,033,358
[45] Date of Patent: Mar. 7, 2000

[54] BIOLOGICAL SPECIMEN CONTAIMENT ARRANGEMENT

[75] Inventors: William Charles Mers Kelly, Crestwood; William Alexander Reuss, Jr., Louisville; David Young Phelps, Anchorage, all of Ky.

[73] Assignee: Louisville Laboratories, Louisville, Ky.

[21] Appl. No.: 09/072,160

[22] Filed: May 4, 1998

Related U.S. Application Data

[63] Continuation-in-part of application No. 08/877,523, Jun. 17, 1997, Pat. No. 5,827,174, which is a continuation-in-part of application No. 08/534,051, Sep. 26, 1995, Pat. No. 5,681,742.

[51] Int. Cl.[7] ..................................................... A61B 17/43
[52] U.S. Cl. ............................................ 600/33; 128/898
[58] Field of Search .................................. 600/33, 34, 35; 435/288.4, 288.5; 604/906; 128/898

[56] References Cited

U.S. PATENT DOCUMENTS

| | | | |
|---|---|---|---|
| 4,877,659 | 10/1989 | Vince | 428/34.1 |
| 5,691,194 | 11/1997 | Gordon | 435/287.1 |
| 5,780,294 | 7/1998 | Stevens et al. | 435/297.5 |

*Primary Examiner*—Linda C. M. Dvorak
*Assistant Examiner*—Rosiland Kearney
*Attorney, Agent, or Firm*—Don Halgren

[57] ABSTRACT

The present invention an in vitro fertilization system for the receipt and treatment of an egg comprising a housing having a receiving chamber for the receipt of an egg. The system includes a holding chamber for nesting of the egg within the receiving chamber, and an apparatus for permitting treatment of the egg while the egg is held in the holding chamber. An arrangement is disposed in the housing to permit the egg in the holding chamber to be viewed non-microscopically.

2 Claims, 4 Drawing Sheets

BIOLOGICAL SPECIMEN CONTAIMENT ARRANGEMENT

RELATED APPLICATIONS

This application is a continuation in part of our U.S. patent application Ser. No. 08/877,523 filed Jun. 17, 1997, U.S. Pat. No. 5,827,174 which is a continuation in part application of U.S. patent application Ser. No. 08/534,051, filed Sep. 26, 1995, U.S. Pat. No. 5,681,742 each of which is incorporated herein by reference, in their entirety.

FIELD OF THE INVENTION

This invention relates to biological specimen containment devices and more particularly to an arrangement of chambers useful for in vitro fertilization cultures.

PRIOR ART

Containment devices for biological specimens are often restricted in their design function. The devices often must not permit atmosphere to strike the medium within the container. The device must not have sharp edges that will bind or unintentionally agitate the medium (embryo/culture) within the container. The device must also often permit the medium to be maintained at a desired precise temperature and the device must often minimize the exposure of the medium to the atmosphere.

It is an object to the present invention to provide an in vitro fertilization chamber arrangement to permit a viewing of the genetic material comprising its contents, while minimizing handling and permitting viewing thereof, without a microscope or without opening the chamber containing the genetic material and exposing it to the atmosphere.

It is a further object of the present invention, to provide a closed in vitro fertilization system, which will permit the fertilization of an egg, within a closed system, and to readily permit inspection and retrieval of that fertilized egg.

It is yet a further object of the present invention, to provide a chamber arrangement, wherein an egg may be readily retrieved with minimum likelihood of damage thereto.

BRIEF SUMMARY OF THE INVENTION

The present invention relates to an arrangement of biological specimen containment devices adapted to permit intravaginal placement of fertilized ovocytes. In a first embodiment of the present invention, an in vitro fertilization lens chamber may be molded from a clear $CO_2$ permeable clear polymer. Such a lens chamber comprises a housing having a lower planar base, the housing defining an inner chamber. The inner chamber is sealed, and has an access port on an upper surface thereof. The upper surface access port is openable so as to permit the introduction of an egg and or culture medium into the inner chamber. The inner chamber has smooth slopping walls, having a lowermost necked down holding chamber at its lowermost end. The access port and the holding chamber at the lowermost end of the housing are preferably in vertical alignment. A lens is arranged through the sidewall of the chamber housing, its focal point being in alignment with the holding chamber at the base of the inner chamber. The focal point is the necked down area of the inner chamber which is, of course, the holding chamber. The lens permits viewing of an egg and its fertilization and development with a medium disposed within that chamber through the access port along its upper surface. Thus the inner chamber may be filled with a culture media and an egg/sperm may be deposited therewithin, for settlement within that holding chamber. Retrieval of that developing embryo may be facilitated by insertion of a retrieval needle through the access port while viewing that procedure through the lens.

A further embodiment of the closed in vitro fertilization system of the present invention, is comprised of a plurality of contiguous chambers defined between flexible webs of polymeric material. These chambers have frangible ports or gates, to permit the advancement of a medium within one chamber to move to a subsequent chamber without exposure to the atmosphere and without external handling. Such a flexible multi-chamber apparatus may have a generally rectangular pouch, having opposed flexible walls sealed along its generally rectangular periphery. A first port or collection chamber is arranged within that first pouch, to permit an egg to be deposited therewithin. The collection chamber has a sealed wall between it and a second or washing chamber. The sealed wall has a frangible gate between the collection chamber and the wash chamber. Upon receipt and collection of an embryo within the collection chamber, the embryo/egg is isolated, and the frangible gate may be broken by manual manipulation, to permit the egg and a controlled amount of medium to be moved and manually manipulated into the next (wash) chamber. A fertility chamber preferably disposed contiguous and in-fluid communication with the wash chamber, and after a second frangible gate is broken, to permit the washed egg to pass therewithin. The fertility chamber is similarly comprised of a sealed flexible bag element defined by heat sealed or adhesively joined wall segments. An injection port for the introduction of sperm and/or culture media is arranged through a side wall in the fertility chamber. The injection port does not permit the atmosphere to enter therewithin. The fertility chamber is in communication with one or more separate incubation chambers, through a elongated conduit. A frangible or breakable gate is arranged within the wall of the fertility chamber, to permit breaking of that seal gate and passage of an egg and sperm into a subsequent incubation chamber. The incubation chamber is preferably defined by a flexible baglike housing which may have its own injection port, for receipt of culture media therewithin. The incubation chamber is defined by a peripheral wall of sealed resilient material. The incubation chamber has a frangible or sealed breakable gate at one side thereof to permit discharge of a cultured fertilized egg into a subsequent holding chamber allowing for retrieval of that fertilized egg by a catheter or needle retrieval device. The holding chamber has an access port for permitting entry of a catheter or needle into that retrieval chamber. That retrieval chamber has sidewalls which are necked downwardly toward one another, to permit the collection of the fertilized egg into a holding compartment, without damaged thereto. The holding compartment permits safe suspension of the fertilized egg until it may be safely retrieved by that catheter or retrieval needle.

Yet a further holding lens chamber, may be utilized as recited in a further embodiment, wherein the retrieved egg may be inserted into a housing for "IXCY", a type of fertilization procedure. This housing has a planar base for support of the chamber in an upright orientation. This retraining chamber has smooth walls and is fully enclosed, but for a needle guide or an access port on an upper surface thereof. The walls of the chamber have a lower end, which are sloped so as to angle downwardly to a holding chamber at its lowermost end, the size of the holding chamber at the lower most end is such, so as to permit a close fitting arrangement with an isolated egg to allow injection or other treatment to take place. The holding chamber is preferably in longitudinal and vertical alignment with the access port, to permit a needle or catheter to enter therewithin for safe retrieval and/or access to that fertilized egg.

A further embodiment of the present invention is shown in a fertilization containment needle arrangement having a needle tip which is in a fluid communication within an enlarged retainment chamber therewithin. The needle and the retrainment chamber are in communication with a conduit and suction source at a second end of the retainment chamber. A light source, such a fiberoptic means, is arranged annularly around the suction conduit, to permit a full delivery of light within the retrieval chamber. The needle is used to access an egg from a female. The light source is utilized for elimination, to permit analysis of the retrieved egg and fluid and debris from the female. The suction conduit into the retrieval chamber, permits suction removal of the debris and unwanted fluid from the captured egg. Such a needle apparatus may then be utilized to deliver the retrieved egg, and any desired culture medium and/or sperm subsequently introduced into the retrieval chamber, into a holding chamber as identified hereinabove.

The invention thus comprises an in vitro fertilization system for the receipt and treatment of an egg comprising: a housing having a receiving chamber for the receipt of an egg; a holding chamber for nesting of the egg within the receiving chamber; an apparatus for permitting treatment of the egg while the egg is held in the holding chamber; and an arrangement disposed in said housing to permit the egg in the holding chamber to be viewed non-microscopically. The arrangement in the housing may comprise a lens disposed within a side wall of the housing. The arrangement may comprise a light source arranged within said housing and disposed about said holding chamber. The apparatus for permitting treatment may comprise at least one flexible walled chamber having at least one port therein for admission of a treatment medium therethrough. The chamber may include a frangible gate for permitting passage of a treated egg therethrough. A plurality of successive flexible walled chambers may be in fluid communication with one another upon breaking a sealing of the frangible gate, to permit successive treatment of an egg therein. The invention also includes a method of treating an egg in an in vitro fertilization process, comprising the steps of: providing a plurality of separate chambers within a flexible walled pouch containment apparatus; forming a breakable gate between adjacent chambers; installing an entry port through a wall of at least one of the chambers; introducing an egg and a medium into a first chambers; and breaking the gate in the first chamber to permit the egg therein to be fluidly communicated into an adjacent chamber for successive treatment thereof, and providing a first treatment of the egg in the first chamber; and providing a second treatment of the egg in a second chamber.

BRIEF DESCRIPTION OF THE DRAWINGS

The objects and advantages of the present invention will become more apparent, when viewed in conjunction with the following drawings, in which:

FIG. 4 is a side elevational view of retrieval needle apparatus for the retrieval and separation of an egg prior to its introduction into a subsequent invetro fertilization chamber or the like.

DESCRIPTION OF THE PREFERRED EMBODIMENTS

Figure 1:
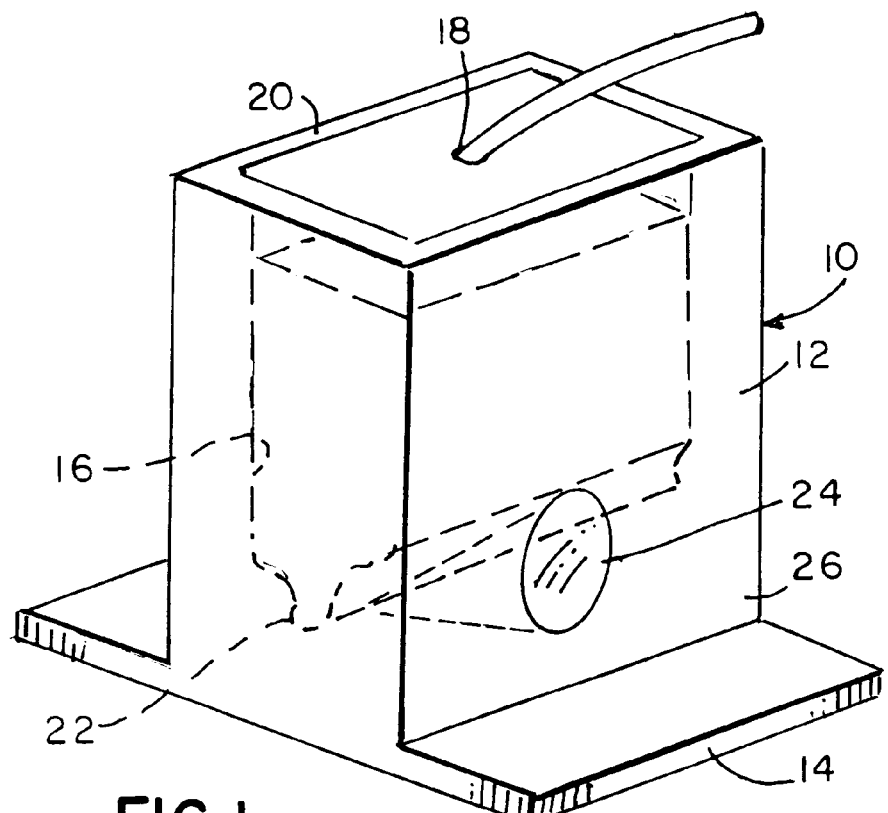
FIG. 1 is a perspective view of an in vitro fertilization lens chamber constructed according to the principles of the present invention.
Figure 1A:
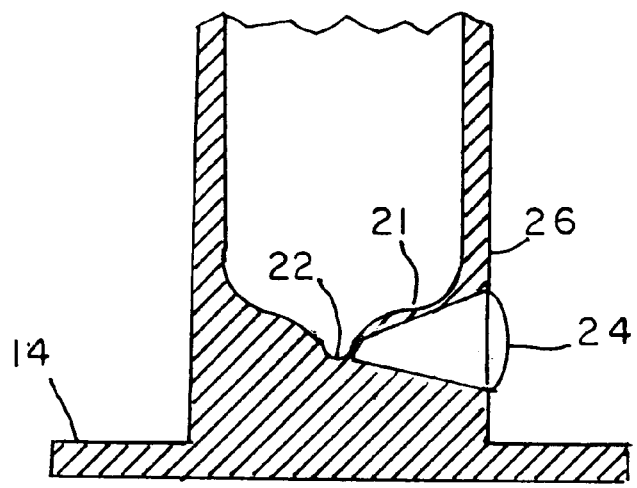
FIG. 1a is a sectional view taken along the lines 1a—1a of FIG. 1.

Referring to the drawings in detail, and particularly to FIG. 1, there is shown a first embodiment of the present invention comprising an arrangement of a biological specimen containment device 10 adapted to permit intravaginal placement of fertilized ovocytes. In a first embodiment of the present invention, as shown in FIG. 1, an in vitro fertilization lens chamber 12 may be molded from a clear $CO_2$ permeable polymer. Such a lens chamber 12 comprises a housing having a lower planar base 14, the housing defining an inner chamber 16. The inner chamber 16 is sealed, and has an openable access port 18 on an upper surface 20 thereof. The upper surface access port 18 is openable so as to permit the introduction of an egg and or culture medium into the inner chamber 16. The inner chamber 16 has smooth slopping walls 21, having a lowermost necked down holding chamber 22 at its lowermost end, as may be seen in FIG. 1a. The access port 18 and the holding chamber 22 at the lowermost end of the housing are preferably in vertical alignment. A lens 24 is arranged through the sidewall 26 of the chamber housing, its focal point being in alignment with the holding chamber 22 at the base of the inner chamber 16, as may be seen in FIG. 1. The focal point is the necked down area of the inner chamber 16, which is, of course, the holding chamber 22. The lens 24 permits viewing of an egg and its fertilization and development with a medium disposed within that chamber through the access port along its upper surface. Thus the inner chamber 16 may be filled with a culture media and an egg/sperm may be deposited therewithin, for settlement within that holding chamber 22. Retrieval of that developing embryo may be facilitated by insertion of a retrieval needle through the access port 18 while viewing that procedure through the lens 24.

Figure 2:
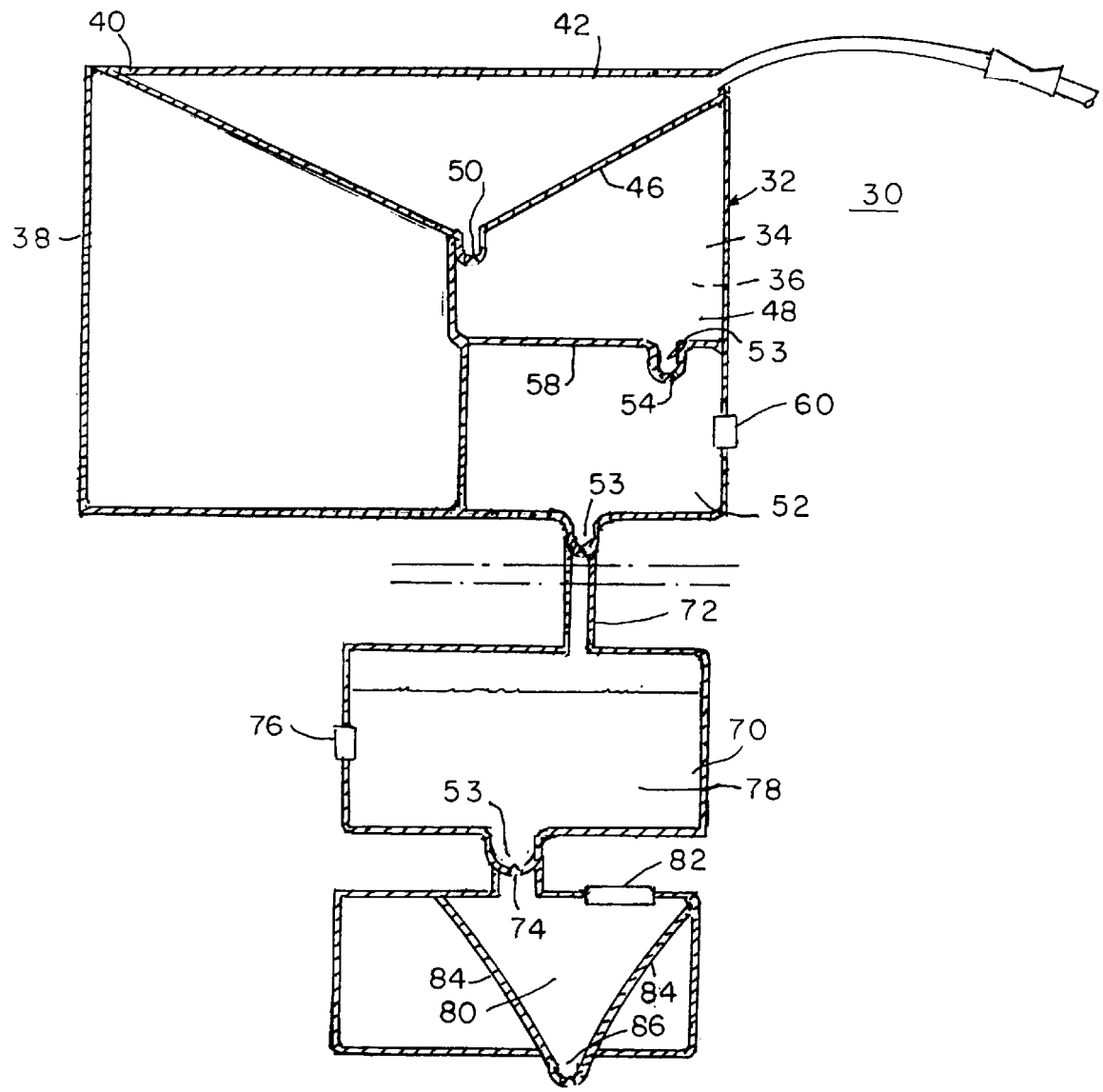
FIG. 2 is a plan view of a closed in vitro fertilization system showing the multiple chambers in communication with one another, according to the principles of the present invention.

A further embodiment of the closed in vitro fertilization system of the present invention is shown in FIG. 2, wherein a fertilization system 30 is comprised of a plurality of contiguous chambers 32 defined between flexible webs 34 and 36 of polymeric material. These chambers 32 have frangible ports or gates, to permit the advancement of a medium within one chamber to move to a subsequent chamber without exposure to the atmosphere. Such a flexible multi-chamber apparatus 30 may have a generally rectangular pouch 38, having opposed flexible walls 34 and 36 sealed along its generally rectangular periphery 40. A first port or collection chamber 42 is arranged within that first pouch 40, to permit an egg to be deposited therewithin by a needle, catheter or syringe, not shown. The collection chamber 42 has a sealed wall 46 between it and a second or washing chamber 48. The sealed wall 46 has a frangible gate 50 between the collection chamber 42 and the wash chamber 48. Upon receipt and collection of an embryo within the collection chamber 42, the frangible gate 50 may be broken by manual manipulation, to permit the egg and medium to be moved and manually manipulated into the next (wash) chamber 48. A fertility chamber 52 preferably disposed contiguous and in-fluid communication with the wash chamber 48, and after a second frangible gate 54 is broken, to permit the washed egg to pass therewithin. Each gate 50 and/or 54 et seq. are arranged adjacent a "holding cavity" 53 for receipt of the egg. The fertility chamber 52 is similarly comprised of a sealed flexible bag element defined by heat sealed or adhesively joined wall segments 58. An injection port 60 for the introduction of sperm and/or culture media is arranged through a side wall 62 in the fertility chamber 52. The injection port 62 does not permit the atmosphere to enter therewithin. The fertility chamber 52 is in communication with one or more separate incubation chambers 70, (only one shown here for clarity), through a elongated flexible conduit 72. A frangible or breakable gate 74 is arranged within the wall of the fertility chamber, to permit breaking of that seal gate and passage of an egg and sperm into a subsequent incubation chamber. The incubation chamber 70 is preferably defined by a flexible baglike housing which may have its own injection port 76, for receipt of culture media therewithin. The incubation chamber 70 is defined by a peripheral wall of sealed resilient material 78. The frangible or sealed breakable gate 74 at one side of the chamber 70 permits discharge of a cultured fertilized egg into a subsequent holding chamber 80, permitting retrieval of that fertilized egg from that "holding" chamber" 80, by a catheter or needle retrieval device, not shown, for clarity. The holding chamber 80 has an access port 82 for permitting entry of a catheter or needle into that retrieval chamber. That retrieval chamber 80 has sidewalls 84 which are necked downwardly toward one another, to permit the collection of the fertilized egg into a conically shaped holding compartment 86, without damaged thereto. The holding compartment 86 permits safe suspension of the fertilized egg until it may be safely retrieved by that catheter or retrieval needle.

Figure 3:
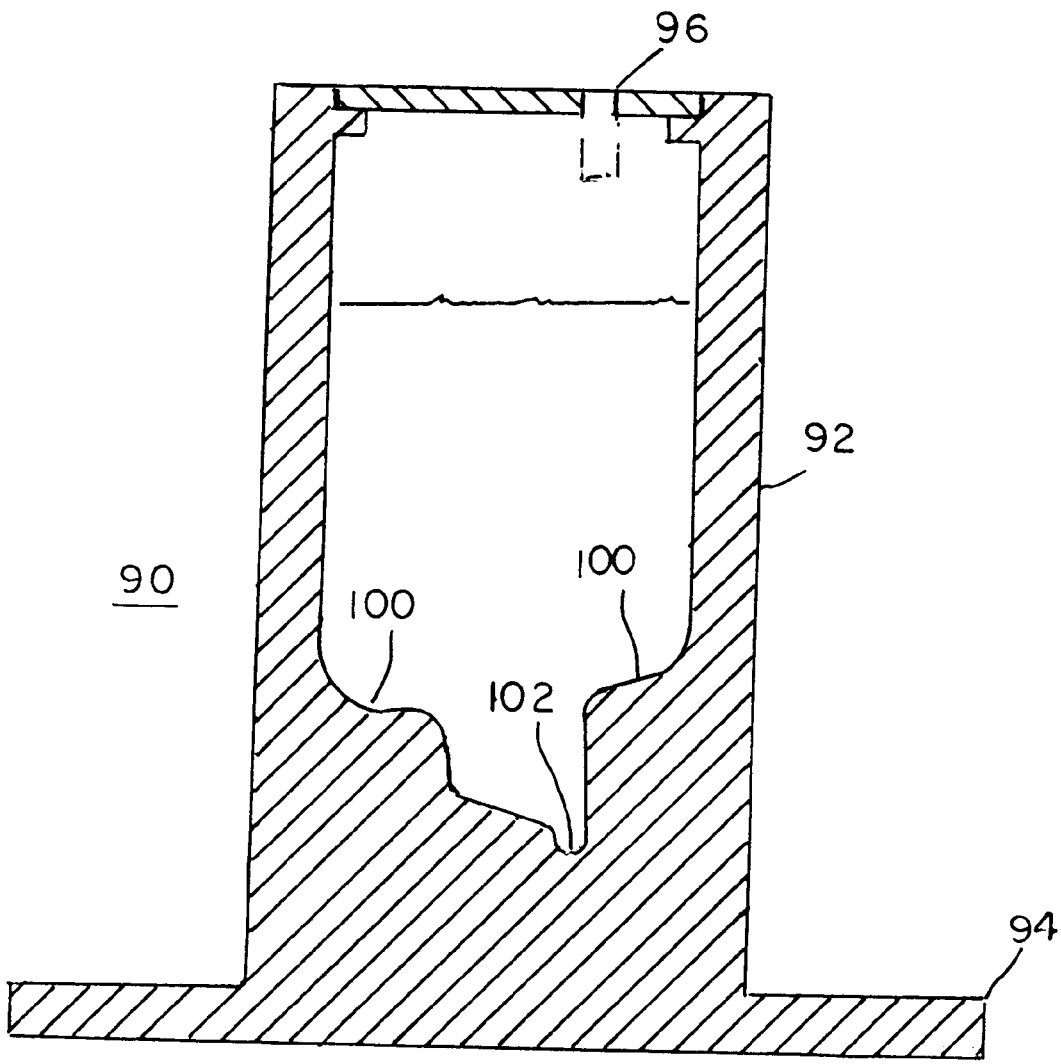
FIG. 3 is a holding chamber for "IXCY", constructed according to the principles of the present invention.

Yet a further fertilization system holding lens chamber 90 is shown in FIG. 3, may be utilized as recited in a further embodiment, wherein the retrieved egg may be inserted into a housing 92 for an "IXCY" procedure. This housing 92 has a planar base 94 for support of the chamber 90 in an upright orientation. This retraining chamber 90 has smooth internal walls 96 and is fully enclosed, but for a piercable or openable needle guide or an access port 96 on an upper walled surface 98 thereof. The walls of the chamber 90 have a lower end 100, which are sloped so as to angle downwardly to a holding chamber 102 at its lowermost end. The size of the holding chamber 102 at the lowermost end is such, so as to permit a close fitting arrangement with a fertilized egg disposed therein. The holding chamber 102 is preferably in longitudinal and vertical alignment with the access port 96, to permit separation of the egg from the debris and media and to remain basically segregated therefrom, and also permit a needle or catheter to enter therewithin for safe retrieval and/or access to that fertilized egg.

Figure 4:
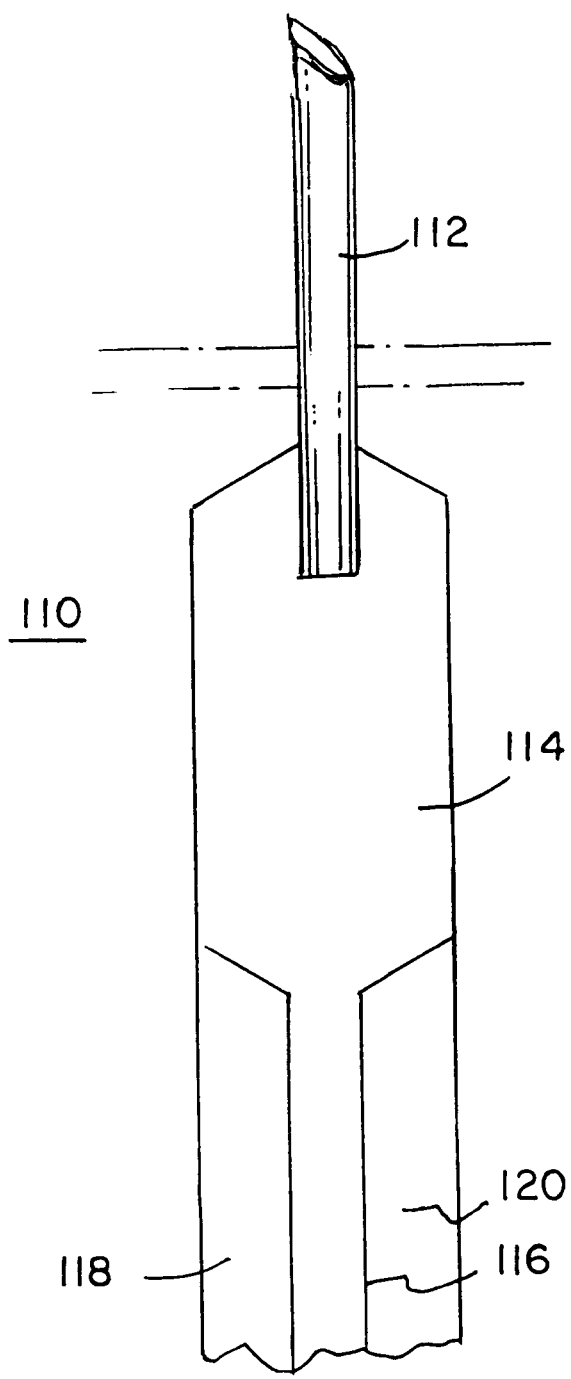

A further embodiment of the present invention is shown in FIG. 4, as a fertilization containment needle arrangement 110 having a needle tip 112 which is in fluid communication within an enlarged retainment chamber 114 therewithin. The needle and the retainment chamber 114 are in communication with a conduit and suction source 116 at a second end 118 of the retainment chamber 114. A light source 120, such a fiberoptic means, is arranged annularly around the suction conduit 116, to permit a full delivery of light within the retrieval chamber 114. The needle 110 is used to access an egg from a female. The light source 118 is utilized for content examination, to permit analysis of the retrieved egg and fluid and debris from the female. The suction conduit 116 into the retrieval chamber 114, permits suction removal of the debris and unwanted fluid from the captured egg. Such a needle apparatus 110 may then be utilized to deliver the retrieved egg, and any desired culture medium and/or sperm subsequently introduced into the retrieval chamber, into a holding chamber 19, 30 and/or 90 as identified in the figures recited hereinabove.

We claim:

1. A method of treating an egg in an in vitro fertilization process, comprising the steps of:

providing a plurality of separate chambers within a flexible walled pouch containment apparatus;

forming a breakable gate between adjacent chambers;

installing an entry port through a wall of at least one of said chambers;

introducing an egg and a medium into a first of said chambers; and breaking said gate in said first of said chambers to permit said egg therein to be communicated into an adjacent chamber for successive treatment thereof.

2. The method as recited in claim 1, including the steps of:

providing a first treatment of said egg in said first chamber; and providing a second treatment of said egg in a second of said chambers.

* * * * *